United States Patent
Katsuhara et al.

(10) Patent No.: US 10,765,391 B2
(45) Date of Patent: Sep. 8, 2020

(54) DYNAMIC ANALYSIS SYSTEM

(71) Applicant: Konica Minolta, Inc., Tokyo (JP)

(72) Inventors: Shinsuke Katsuhara, Kodaira (JP); Shikou Kaneko, Niiza (JP); Keiko Itaya, Hino (JP); Akinori Tsunomori, Kodaira (JP)

(73) Assignee: KONICA MINOLTA, INC., Tokyo (JP)

( * ) Notice: Subject to any disclaimer, the term of this patent is extended or adjusted under 35 U.S.C. 154(b) by 171 days.

(21) Appl. No.: 15/888,489

(22) Filed: Feb. 5, 2018

(65) Prior Publication Data
US 2018/0228458 A1  Aug. 16, 2018

(30) Foreign Application Priority Data

Feb. 15, 2017  (JP) ................... 2017-025509

(51) Int. Cl.
*G06K 9/00* (2006.01)
*A61B 6/00* (2006.01)
(Continued)

(52) U.S. Cl.
CPC ............ *A61B 6/5205* (2013.01); *A61B 5/021* (2013.01); *A61B 5/024* (2013.01); *A61B 5/0205* (2013.01);
(Continued)

(58) Field of Classification Search
CPC ..... A61B 6/5205; A61B 5/0205; A61B 5/021; A61B 5/024; A61B 5/0816; A61B 5/14542
See application file for complete search history.

(56) References Cited

U.S. PATENT DOCUMENTS 5,359,513 A * 10/1994 Kano ................... G06T 3/0081
128/922
6,443,907 B1 * 9/2002 Mansy ..................... A61B 7/04
600/529
(Continued)

FOREIGN PATENT DOCUMENTS

JP   2005537068 A   12/2005
JP   2006-239195 A   9/2006
(Continued)

OTHER PUBLICATIONS

JPO, Office Action for the corresponding Japanese patent application No. 2017-025509, dated May 26, 2020, with English translation.

*Primary Examiner* — Shefali D Goradia
(74) *Attorney, Agent, or Firm* — Lucas & Mercanti, LLP (57) ABSTRACT

A dynamic analysis system includes a hardware processor. A first plurality of frame images showing a dynamic state of a chest of an intubated first examinee is obtained by radiation imaging of the chest of the first examinee. Based on the first plurality of frame images, the hardware processor calculates a signal value change amount and/or a shape change amount of a predetermined structure of the chest in the first plurality of frame images. Based on the calculated signal value change amount and/or shape change amount, the hardware processor generates assessment information to assess a respiratory status of the first examinee at time of intubation or extubation.

12 Claims, 5 Drawing Sheets

(51) Int. Cl.
 *A61B 5/145* (2006.01)
 *A61B 5/08* (2006.01)
 *A61B 5/024* (2006.01)
 *A61B 5/021* (2006.01)
 *A61B 5/0205* (2006.01)

(52) U.S. Cl.
 CPC ......... *A61B 5/0816* (2013.01); *A61B 5/14542* (2013.01); *A61B 6/487* (2013.01)

(56) References Cited

U.S. PATENT DOCUMENTS

| | | | |
|---|---|---|---|
| 6,997,880 B2* | 2/2006 | Carlebach | A61B 5/0836 600/311 |
| 8,219,180 B2* | 7/2012 | Cao | A61B 5/06 600/117 |
| 2005/0244044 A1* | 11/2005 | Inoue | A61B 6/4233 382/132 |
| 2012/0041279 A1* | 2/2012 | Freeman | A61B 5/0205 600/301 |
| 2017/0014093 A1* | 1/2017 | Hosoki | A61B 6/54 |
| 2018/0280646 A1* | 10/2018 | Freeman | A61M 16/024 |

FOREIGN PATENT DOCUMENTS

| | | |
|---|---|---|
| JP | 2011-510784 A | 4/2011 |
| JP | 2014-502854 A | 2/2014 |

* cited by examiner

DYNAMIC ANALYSIS SYSTEM

BACKGROUND

1. Technological Field

This invention relates to a dynamic analysis system.

2. Description of the Related Art

There has been proposed a technique for, with an adaptive mathematical model, non-invasively obtaining estimates of physiologic breathing effort and imposed breathing effort of a patient connected to a ventilator from data obtained from an airway pressure sensor and an airway flow sensor attached to the patient. (Refer to, for example, Japanese Patent Application Publication (Translation of PCT Application) No. 2005-537068.)

According to the ventilator weaning protocols of the Japanese Society of Intensive Care Medicine, at the time of extubation (i.e. removal from a ventilator), the respiratory status of the patient needs to be assessed with vital information (respiratory rate, $SpO_2$, etc.) and patient assessment (exacerbation of respiratory pattern, occurrence of paradoxical breathing, use of accessory muscles of respiration, etc.). Preferably, the same assessment is carried out at the time of intubation (i.e. attachment to a ventilator) too.

Patient assessment is, however, subjectively determined by the medical profession, which makes robust assessment of the respiratory status of a patient(s) difficult.

SUMMARY

Objects of the invention include objectively assessing the respiratory status of a patient(s) at the time of intubation and extubation.

To achieve at least one of the abovementioned objects, according to an aspect of the invention, there is provided a dynamic analysis system including a hardware processor that: based on a first plurality of frame images showing a dynamic state of a chest of an intubated first examinee obtained by radiation imaging of the chest of the first examinee, calculates a signal value change amount and/or a shape change amount of a predetermined structure of the chest in the first plurality of frame images; and based on the calculated signal value change amount and/or shape change amount, generates assessment information to assess a respiratory status of the first examinee at time of intubation or extubation.

According to another aspect of the invention, there is provided a dynamic analysis system including a hardware processor that: based on a plurality of frame images showing a dynamic state of a chest of a first examinee obtained by radiation imaging of the chest of the first examinee, calculates a signal value change amount and/or a shape change amount of a predetermined structure of the chest in the plurality of frame images; and compares the calculated signal value change amount and/or shape change amount with statistical data of the signal value change amount and/or the shape change amount calculated about a second examinee who has been intubated or extubated in a past, thereby generating a result of the comparison as assessment information to assess a respiratory status of the first examinee at time of intubation or extubation.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the invention, wherein.

DETAILED DESCRIPTION OF EMBODIMENTS

Hereinafter, one or more embodiments of the invention will be described with reference to the drawings. However, the scope of the invention is not limited to the disclosed embodiments.

First Embodiment (Configuration of Dynamic Analysis System 100)

First, configuration of a first embodiment of the invention is described.

Figure 1:
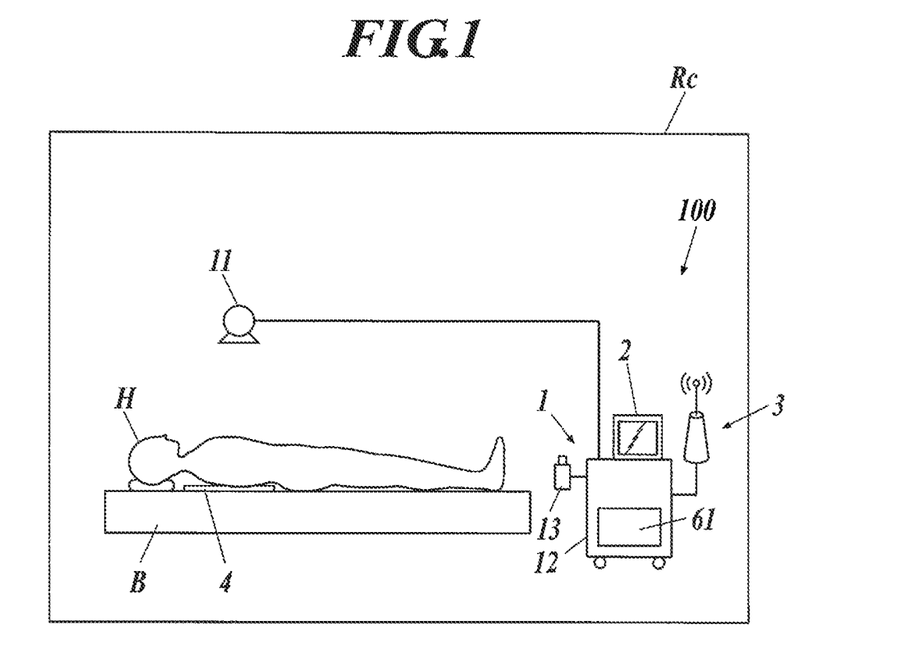
FIG. 1 shows overall configuration of a dynamic analysis system according to one or more embodiments.

FIG. 1 shows an example of overall configuration of a dynamic analysis system 100 according to the embodiment(s).

The dynamic analysis system 100 is, for example, a visiting system to take images of a patient as a subject who is in an ICU, an operation room or the like and difficult to move. The dynamic analysis system 100 includes a radiation generator 1, a console 2, an access point 3 and an FPD (Flat Panel Detector) cassette 4. The radiation generator 1 has wheels and is configured as a movable visiting cart provided with the console 2 and the access point 3. In the dynamic analysis system 100, the console 2 can be connected and communicate with the radiation generator 1 and the FPD cassette 4 through the access point 3.

The dynamic analysis system 100 is, as shown in FIG. 1, a system that is brought into an operation room (or ICU) Rc or the like, and performs dynamic imaging of an examinee H by emitting radiation from a portable radiation source 11 of the radiation generator 1 in the state in which the FPD cassette 4 is inserted into, for example, between the examinee H who lies down on a bed B and the bed B, or into a not-shown insertion slot on the opposite side of the bed B to the side where the examinee H lies down.

Dynamic imaging is performed by repeatedly emitting pulsed radiation, such as pulsed X-rays, to the examinee H at predetermined time intervals (pulse emission) or continuously emitting radiation without a break to the examinee H at a low dose rate (continuous emission), thereby obtaining a plurality of images. By dynamic imaging, a cyclic dynamic state of the examinee H is imaged. Examples of the dynamic state include: change in shape of the lungs by expansion and contraction of the lungs with breathing; and pulsation of the heart. A series of images obtained by this continuous imaging is called a dynamic image. Images constituting a dynamic image are called frame images.

In this embodiment, the dynamic analysis system 100 images the dynamic state of the chest of the examinee H.

Hereinafter, apparatuses of the dynamic analysis system 100 are described.

The radiation generator 1 is a radiation generator that can perform at least one of the pulse emission and the continuous emission. The radiation generator 1 includes the radiation source 11 that emits radiation, a radiation emission controller 12 and an exposure switch 13.

The radiation source 11 emits radiation (X-rays) to the examinee H under the control of the radiation emission controller 12.

The radiation emission controller 12 controls the radiation source 11 on the basis of radiation emission conditions sent from the console 2 so as to perform imaging with radiation (radiation imaging). The radiation emission conditions input from the console 2 include a tube current, a tube voltage, a frame rate (the number of frame images to be taken per unit time (e.g. one second), the total imaging time or the total number of frame images to be taken per imaging, a type of added filter, and, in the case of the pulse emission, radiation emission time per frame image.

The exposure switch 13 inputs radiation emission command signals to the console 2 by being depressed.

The console 2 outputs the radiation emission conditions to the radiation generator 1 and image reading conditions to the FPD cassette 4 so as to control radiation imaging and reading actions of radiation images, and also, on the basis of a dynamic image(s) sent from the FPD cassette 4, generates and displays assessment information to assess the respiratory status of the examinee H at the time of intubation or extubation of the examinee H.

Figure 2:
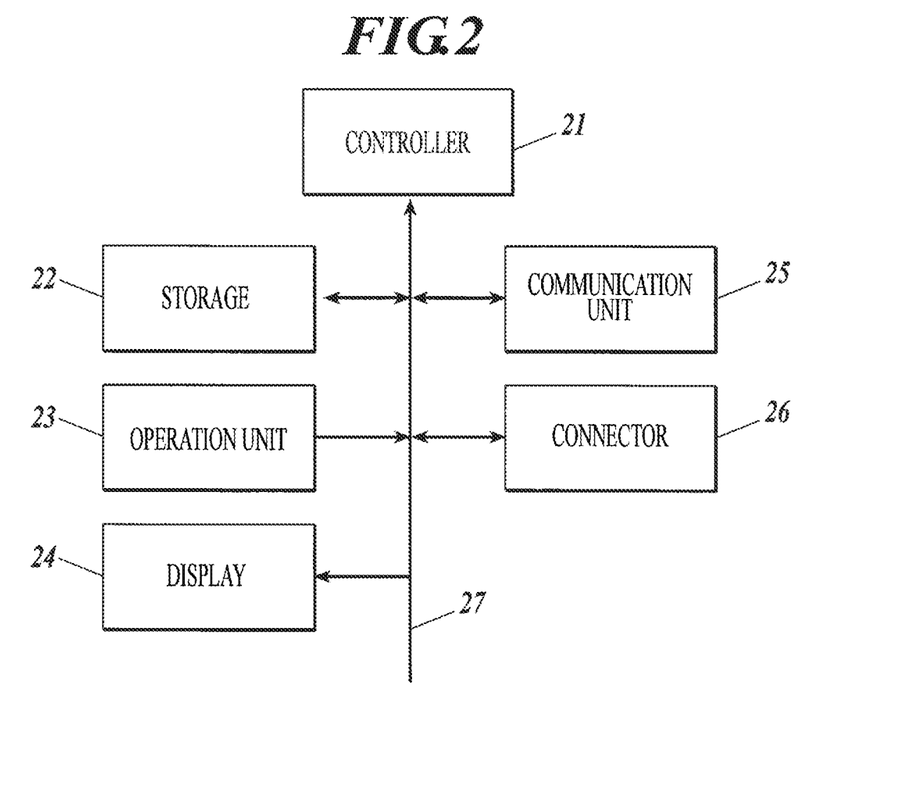
FIG. 2 is a block diagram showing functional configuration of a console shown in FIG. 1.

FIG. 2 shows an example of functional configuration of the console 2. As shown in FIG. 2, the console 2 includes a controller 21, a storage 22, an operation unit 23, a display 24, a communication unit 25 and a connector 26. These units or the like are connected to one another through a bus 27.

The controller 21 includes a CPU (Central Processing Unit; hardware processor) and a RAM (Random Access Memory). The CPU of the controller 21 reads a system program and various process programs stored in the storage 22 in response to operation on the operation unit 23, opens the read programs in the RAM, and, in accordance with the opened programs, performs concentrated control of actions of the units or the like of the console 2 and actions of the radiation generator 1 and the FPD cassette 4. Further, the controller 21 performs various processes including the below-described respiratory status assessment process A in accordance with the opened programs.

The storage 22 is constituted of a nonvolatile semiconductor memory, a hard disk or the like. The storage 22 stores therein various programs to be executed by the controller 21, parameters necessary to perform processes of the programs, data, such as process results, and so forth. For example, the storage 22 stores therein a program to perform the respiratory status assessment process A shown in FIG. 3. The programs are stored in the form of computer readable program code, and the controller 21 acts in accordance with the program code.

The storage 22 also stores therein the radiation emission conditions and the image reading conditions that are used in dynamic imaging. The radiation emission conditions and the image reading conditions can be set by a user operating the operation unit 23.

The storage 22 also stores therein each dynamic image sent from the FPD cassette 4 in such a way as to be associated with, about the examinee H, patient information (attribute information), examination information and vital information at the time of imaging, a shape change amount(s) of a predetermined structure(s) and a signal value change amount(s) calculated on the basis of the dynamic image, and a success/failure result of breathing at the time of intubation (or extubation). The attribute information contains at least one of the age/generation, sex and disease. The vital information contains at least one of the $SpO_2$ value, $PaO_2$ value, heart rate, blood pressure value and respiratory rate.

The storage 22 also stores therein, with respect to each patient group of patients who have the same attribute information and/or vital information among patients who have been intubated in the past, statistical data indicating distributions of the shape change amounts of the predetermined structures and the signal value change amounts before and after intubation about patients who have succeeded in ventilator breathing, and statistical data indicating distributions of the shape change amounts of the predetermined structures and the signal value change amounts before and after intubation about patients who have failed in ventilator breathing. The storage 22 also stores therein, with respect to each patient group of patients who have the same attribute information and/or vital information among patients who have been extubated in the past, statistical data indicating distributions of the shape change amounts of the predetermined structures and the signal value change amounts before and after extubation about patients who have succeeded in spontaneous breathing after extubation, and statistical data indicating distributions of the shape change amounts of the predetermined structures and the signal value change amounts before and after extubation about patients who have failed in spontaneous breathing after extubation.

The statistical data stored in the storage 22 may be generated with respect to each patient group of patients who have the same information on a predetermined one item (e.g. sex) among multiple items (e.g. sex, age/generation, disease, etc.) of the attribute information contained in the patient information, or on a predetermined one item (e.g. respiratory rate) among multiple items (e.g. $SpO_2$ value, $PaO_2$ value, heart rate, blood pressure value, respiratory rate, etc.) of the vital information, or may be generated with respect to each patient group of patients who have the same information on predetermined two or more items (e.g. sex, age/generation and respiratory rate) among multiple times of the attribute information and/or the vital information.

The operation unit 23 includes: a keyboard including cursor keys, number input keys and various function keys; and a pointing device, such as a mouse, and outputs, to the controller 21, command signals input by key operation on the keyboard or by mouse operation. The operation unit 23 may have a touchscreen on the display screen of the display 24. In this case, the operation unit 23 outputs command signals input through the touchscreen to the controller 21.

The display 24 is constituted of a monitor, such as an LCD (Liquid Crystal Display) or a CRT (Cathode Ray Tube), and displays thereon input commands from the operation unit 23, data and so forth in accordance with commands of display signals input from the controller 21.

The communication unit 25 includes a wireless LAN adapter, and controls data sending/receiving to/from the radiation generator 1, the FPD cassette 4 and external apparatuses connected to a communication network, such as a wireless LAN, through the access point 3. Examples of the external apparatuses include a pulse oximeter, a sphygmomanometer and a respiration sensor attached to the examinee H.

The connector 26 is a connector for connection/communications with the FPD cassette 4 through a not-shown cable.

Retuning to FIG. 1, the access point 3 relays communications between the radiation generator 1 and the console 2, communications between the console 2 and the FPD cassette 4, and so forth.

The FPD cassette 4 is a portable radiation detector that can handle dynamic imaging. The FPD cassette 4 is constituted of radiation detection elements arranged in a matrix (two-dimensionally) at predetermined points on a substrate, such as a glass substrate. The radiation detection elements detect radiation (intensity of radiation) emitted from the radiation source 11 and passing through at least the examinee H, convert the detected radiation into electric signals, and accumulate the electric signals therein. The radiation detection elements are connected to TFTs (Thin Film Transistors) or the like that constitute a switching unit. The switching unit controls accumulation and reading of the electric signals into and from the radiation detection elements, so that image data (frame images) are obtained. There are an indirect conversion type FPD that converts radiation into electric signals with photoelectric conversion element(s) through scintillator(s) and a direct conversion type FPD that directly converts radiation into electric signals. Either of them can be used.

The FPD cassette 4 includes: a not-shown reading controller that controls accumulation and reading of the electric signals that are performed by the swinging unit; and a not-shown communication unit to be connected and communicate with the console 2 through the access point 3. The image reading conditions, such as a frame rate, the number of frame images to be taken per imaging and an image size (matrix size), are set by the console 2 through the communication unit. The reading controller controls accumulation and reading of the electric signals into and from the radiation detection elements that are performed by the switching unit. The FPD cassette 4 has a connector so as to be connected and communicate with the console 2 through a not-shown cable.

The FPD cassette 4 may be hand-carried by a radiographer, such as a radiologist. However, because the FPD cassette 4 is relatively heavy and may be broken or damaged if dropped, it can be carried by being inserted into a pocket 61 for a cassette on the visiting cart.

(Actions of Dynamic Analysis System 100)

Next, actions of the dynamic analysis system 100 are described.

Figure 3:
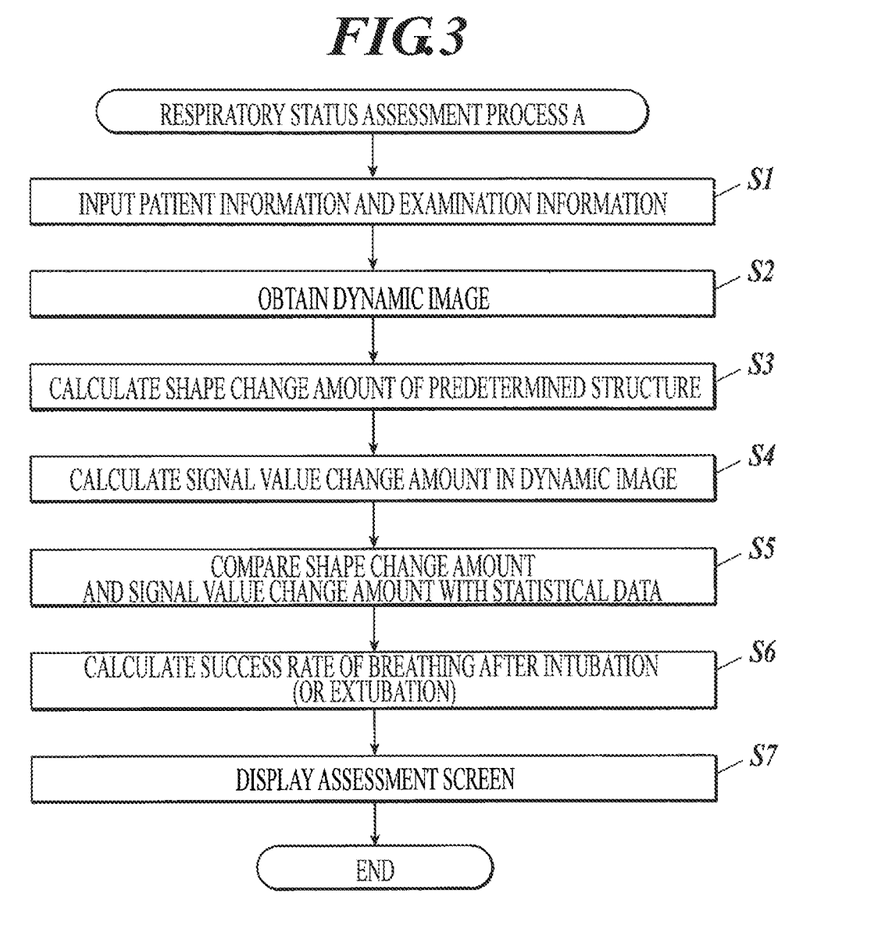
FIG. 3 is a flowchart of a respiratory status assessment process A that is performed by a controller shown in FIG. 2.

FIG. 3 shows flow of the respiratory status assessment process A that is performed by the console 2. The respiratory status assessment process A is performed by the controller 21 working together with the program(s) stored in the storage 22. Hereinafter, the respiratory status assessment process A is described.

First, the controller 21 accepts inputs of patient information (name, age, sex, disease, etc.) and examination information (site to be examined (here, the chest), item for breathing assessment (hereinafter called the "breathing assessment item") (before intubation, after intubation, before extubation, after extubation), etc.) about an examinee H from the operation unit 23 (Step S1).

Next, the controller 21 controls the radiation emission controller 12 and the FPD cassette 4 so that dynamic imaging of the chest of the examinee H is performed in response to a press on the exposure switch 13, and obtains a dynamic image composed of a series of frame images (Step S2).

If the breathing assessment item input in Step S1 is "before intubation", in Step S2, dynamic imaging of the examinee H is performed for several respiratory cycles immediately before the examinee H is intubated. If the breathing assessment item input in Step S1 is "after intubation", in Step S2, dynamic imaging of the examinee H is performed for several respiratory cycles immediately after the examiner H is intubated. If the breathing assessment item input in Step S1 is "before extubation", in Step S2, dynamic imaging of the examinee H is performed for several respiratory cycles immediately before the examinee H is extubated. If the breathing assessment item input in Step S1 is "after extubation", in Step S2, dynamic imaging of the examinee H is performed for several respiratory cycles immediately after the examiner H is extubated.

To the examinee H, a vital information obtaining apparatus(es), such as a pulse oximeter, a sphygmomanometer and/or a respiration sensor, is attached to measure the vital information ($SpO_2$ value, $PaO_2$ value, heart rate, blood pressure value, respiratory rate, etc.) about the examinee H at the time of dynamic imaging (i.e. at the time of intubation or extubation). The measured vital information is input to the console 2 through wireless communications or the like.

A series of frame images of the dynamic image obtained by dynamic imaging is associated and stored with an identification ID to identify the dynamic image, the patient information, the examination information, the radiation emission conditions, the image reading conditions, the vital information at the time of dynamic imaging, the respective numbers indicating what number in the imaging order the respective frame images have been taken, and so forth in the storage 22.

Next, the controller 21 calculates the shape change amount of a predetermined structure of the chest of the examinee H in the obtained dynamic image (Step S3).

In Step S3, the controller 21 first extracts the contour of the predetermined structure from an arbitrary frame image of the dynamic image. Examples of the predetermined structure include lung field(s), diaphragm, bone(s) (e.g. rib(s)) and heart.

The method for extracting the contours of the lung fields is not particularly limited, and any known method can be used. For example, as described in Japanese Patent No. 2987633, in an X-ray image, the image density of the lung field regions corresponding to the right and left lungs is higher than that of their surroundings. Hence, the contours of the lung fields may be extracted by: generating a density histogram of an arbitrary frame image; determining, from the shape or area of the density histogram, image parts of high density regions corresponding to the lung field regions; and extracting the contours of the image parts as the contours of the lung fields. Alternatively, as described in Japanese Patent Application Publication No. 2003-6661, the contours of the lung field regions may be extracted by template matching on an arbitrary frame image with a template defining the contours of the standard lung field regions.

Because, in an X-ray image obtained by imaging the chest from the front, the contours at the bottom of the lung fields are borders between the lung fields and the diaphragm, the contour of the diaphragm may be extracted by extracting the contours at the bottom of the lung fields.

The method for extracting the contours of the ribs is not particularly limited, and any known method can be used. For example, as described in Japanese Patent Application Publication No. H05-176919, the contours of the ribs can be extracted by: setting many contour lines in the lung field regions of an arbitrary frame image in the vertical direction (direction from the head to the feet); fitting a predetermined model function to the contour lines, thereby estimating the contour parts of the rib regions; setting image regions to be processed in the estimated contour parts; obtaining, with respect to each pixel of each image region, the gradient and its orientation by Sobel operator; taking the maximum gradient and its orientation among the pixels of each image region as the gradient and the orientation of the image region; plotting the gradients and their orientations of the respective image regions in a coordinate space as coordinates, thereby forming sets (aggregates) for respective regions, such as the upper edges and the lower edges of the ribs, parts surrounded by the edges of the ribs and parts other than the ribs, in the coordinate space, thereby extracting the image regions classified as the edges, such as the upper edges and the lower edges of the ribs, in the coordinate space as the contours of the rib regions.

The method for extracting the contour of the heart is not particularly limited, and any known method can be used. For example, the contour of the heart region is extracted by: storing a template heart image in the storage 22 beforehand, extracting the heart region in an arbitrary frame image by temperate matching with the template heart image; and extracting its contour as the contour of the heart region.

Figure 4:
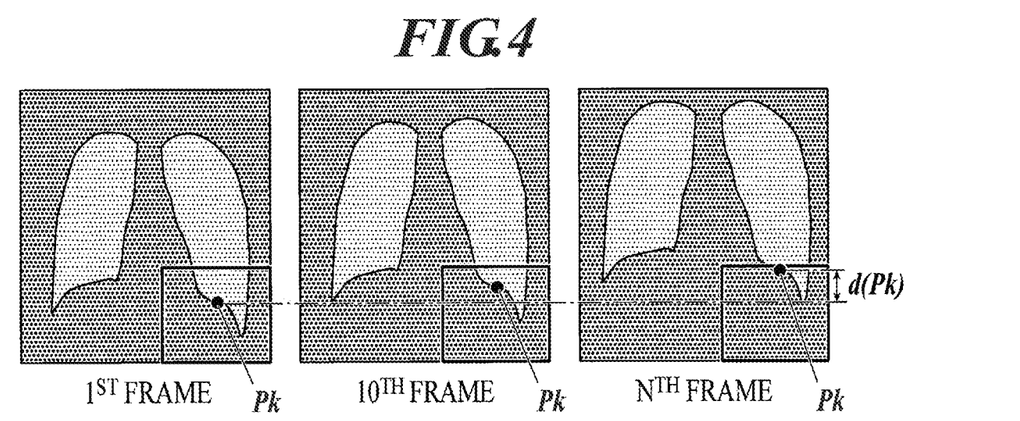
FIG. 4 is a diagram to explain a method for calculating displacement of the diaphragm.

When extracting the contour of the predetermined structure from the arbitrary frame image, the controller 21 sets one or more reference points on the extracted contour, and extracts the reference point(s) in the other frame images by template matching with a predetermined-size region(s) centered at the set reference point(s) as a template image(s). The controller 21 calculates the displacement of the reference point between the frame images as the shape change amount of the predetermined structure. If one reference point is set, and, as shown in FIG. 4, the displacement of a reference point Pk from the first frame image to the $N^{th}$ frame image is the largest in all the frame images, the displacement d(Pk) from the reference point Pk of the first frame image to the reference point Pk of the $N^{th}$ frame image is calculated as the shape change amount, for example. If two or more reference points are set, the mean of the maximum displacements of the respective reference points is calculated as the shape change amount, for example.

Next, the controller 21 calculates the signal value change amount(s) in the obtained dynamic image (Step S4).

In Step S4, the controller 21 calculates the signal value change amount due to perfusion and the signal value change amount due to ventilation in the obtained dynamic image, for example.

In order to calculate the signal value change amount due to perfusion, the controller 21 first calculates, with respect to each frame image, a representative value (e.g. mean, median, maximum, etc.) of pixel signal values (density values) of a lung field region(s), and performs filtering on change with time in the calculated representative value with a time-direction high-pass filter (e.g. a cutoff frequency of 0.80 Hz). This can remove the low frequency component due to ventilation or the like, and obtain the change with time in the signal component due to perfusion. The controller 21 calculates the amplitude value (difference between the local maximum and the local minimum of a cycle) or the mean of the amplitude values of the obtained change with time as the signal value change amount. The controller 21 may perform the filtering on the change with time in the pixel signal values (the representative value) with a time-direction bandpass filter (e.g. a lower limit cutoff frequency of 0.8 Hz and an upper limit cutoff frequency of 2.4 Hz).

In order to calculate the signal value change amount due to ventilation, the controller 21 first calculates, with respect to each frame image, a representative value (e.g. mean, median, maximum, etc.) of pixel signal values (density values) of a lung field region(s), and performs filtering on change with time in the calculated representative value with a time-direction low-pass filter (e.g. a cutoff frequency of 0.80 Hz). This can remove the high frequency component due to perfusion or the like, and obtain the change with time in the signal component due to ventilation. The controller 21 calculates the amplitude value (difference between the local maximum and the local minimum of a cycle) or the mean of the amplitude values of the obtained change with time as the signal value change amount.

Next, the controller 21 compares the shape change amount calculated in Step S3 and the signal value change amounts calculated in Step S4 with the statistical data of the shape change amount and the signal value change amounts about other patients (other examinees) who have the same attribute information and/or vital information as the examinee H (Step S5).

For example, if the breathing assessment item input in Step S1 is "before intubation", the controller 21 reads, from the storage 22 and on the basis of the patient information obtained in Step S1 and/or the vital information obtained at the time of dynamic imaging in Step S2 about the examinee H, the statistical data indicating the distributions of the shape change amount and the signal value change amounts before intubation about other patients who have the same attribute information and/or vital information as the examinee H and have been intubated in the past (the statistical data about the patients who have succeeded in ventilator breathing and the statistical data about the patients who have failed in ventilator breathing). The controller 21 compares the calculated shape change amount and signal value change amounts with the read statistical data. In this embodiment, on histograms of the read statistical data of the shape change amount and the signal value change amounts, positions of the calculation results in Steps S3 and S4 are set (displayed). Note that "(other) patients who have the same attribute information and/or vital information as the examinee H" means, if the information is expressed by numerical value, patients who have the same numerical value as the examinee H or who have numerical values within a certain range that includes the numerical value of the examinee H. (The same applies hereinafter.)

For example, if the breathing assessment item input in Step S1 is "after intubation", the controller 21 reads, from the storage 22 and on the basis of the patient information obtained in Step S1 and/or the vital information obtained at the time of dynamic imaging in Step S2 about the examinee H, the statistical data indicating the distributions of the shape change amount and the signal value change amounts after intubation about other patients who have the same attribute information and/or vital information as the examinee H and have been intubated in the past (the statistical data about the patients who have succeeded in ventilator breathing and the statistical data about the patients who have failed in ventilator breathing). The controller 21 compares the calculated shape change amount and signal value change amounts with the read statistical data. In this embodiment, on histograms of the read statistical data of the shape change amount and the signal value change amounts, positions of the calculation results in Steps S3 and S4 are set (displayed).

For example, if the breathing assessment item input in Step S1 is "before extubation", the controller 21 reads, from the storage 22 and on the basis of the patient information obtained in Step S1 and/or the vital information obtained at the time of dynamic imaging in Step S2 about the examinee H, the statistical data indicating the distributions of the shape change amount and the signal value change amounts before extubation about other patients who have the same attribute information and/or vital information as the examinee H and have been extubated in the past (the statistical data about the patients who have succeeded in spontaneous breathing after extubation and the statistical data about the patients who have failed in spontaneous breathing after extubation). The controller 21 compares the calculated shape change amount and signal value change amounts with the read statistical data. In this embodiment, on histograms of the read statistical data of the shape change amount and the signal value change amounts, positions of the calculation results in Steps S3 and S4 are set (displayed).

For example, if the breathing assessment item input in Step S1 is "after extubation", the controller 21 reads, from the storage 22 and on the basis of the patient information obtained in Step S1 and/or the vital information obtained at the time of dynamic imaging in Step S2 about the examinee H, the statistical data indicating the distributions of the shape change amount and the signal value change amounts after extubation about other patients who have the same attribute information and/or vital information as the examinee H and have been extubated in the past (the statistical data about the patients who have succeeded in spontaneous breathing after extubation and the statistical data about the patients who have failed in spontaneous breathing after extubation). The controller 21 compares the calculated shape change amount and signal value change amounts with the read statistical data. In this embodiment, on histograms of the read statistical data of the shape change amount and the signal value change amounts, positions of the calculation results in Steps S3 and S4 are set (displayed).

The shape change amount calculated in Step S3 and the signal value change amounts calculated in Step S4 may be compared with the statistical data of the shape change amount and the signal value change amounts about all the patients who have been intubated (or extubated) in the past. However, comparing these calculated amounts with the statistical data of the shape change amount and the signal value change amounts about, among all the patients, the patients who have the same attribute information and/or vital information as the examinee H enables the assessment with variation in sex, generation and vital status taken into account.

Next, the controller 21 calculates the success rate of breathing after intubation (or extubation) for the examinee H with a machine learning classifier of deep neural networks or the like (Step S6).

For example, if the breathing assessment item input in Step S1 is "before (or after) intubation", the controller 21 calculates the success rate of ventilator breathing for the examinee H by inputting the attribute information obtained in Step S1 and/or the vital information obtained in Step S2, and the shape change amount and the signal value change amounts before (or after) intubation calculated in Step S3 and Step S4, respectively, about the examinee H, into the classifier of deep neural networks or the like trained with, as feature amounts, the attribute information and/or the vital information, the shape change amount and the signal value change amounts before (or after) intubation, and data of the success/failure result of ventilator breathing about each patient who has been intubated in the past, which are stored in the storage 22.

For example, if the breathing assessment item input in Step S1 is "before (or after) extubation", the controller 21 calculates the success rate of spontaneous breathing after extubation for the examinee H by inputting the attribute information obtained in Step S1 and/or the vital information obtained in Step S2, and the shape change amount and the signal value change amounts before (or after) extubation calculated in Step S3 and Step S4, respectively, about the examinee H, into the classifier of deep neural networks or the like trained with, as feature amounts, the attribute information and/or the vital information, the shape change amount and the signal value change amounts before (or after) extubation, and data of the success/failure result of spontaneous breathing after extubation about each patient who has been extubated in the past, which are stored in the storage 22.

Next, the controller 21 displays, on the display 24, an assessment screen 241 that contains the comparison result in Step S5 and the calculation result in Step S6 (Step S7), and ends the respiratory status assessment process A.

Figure 5:
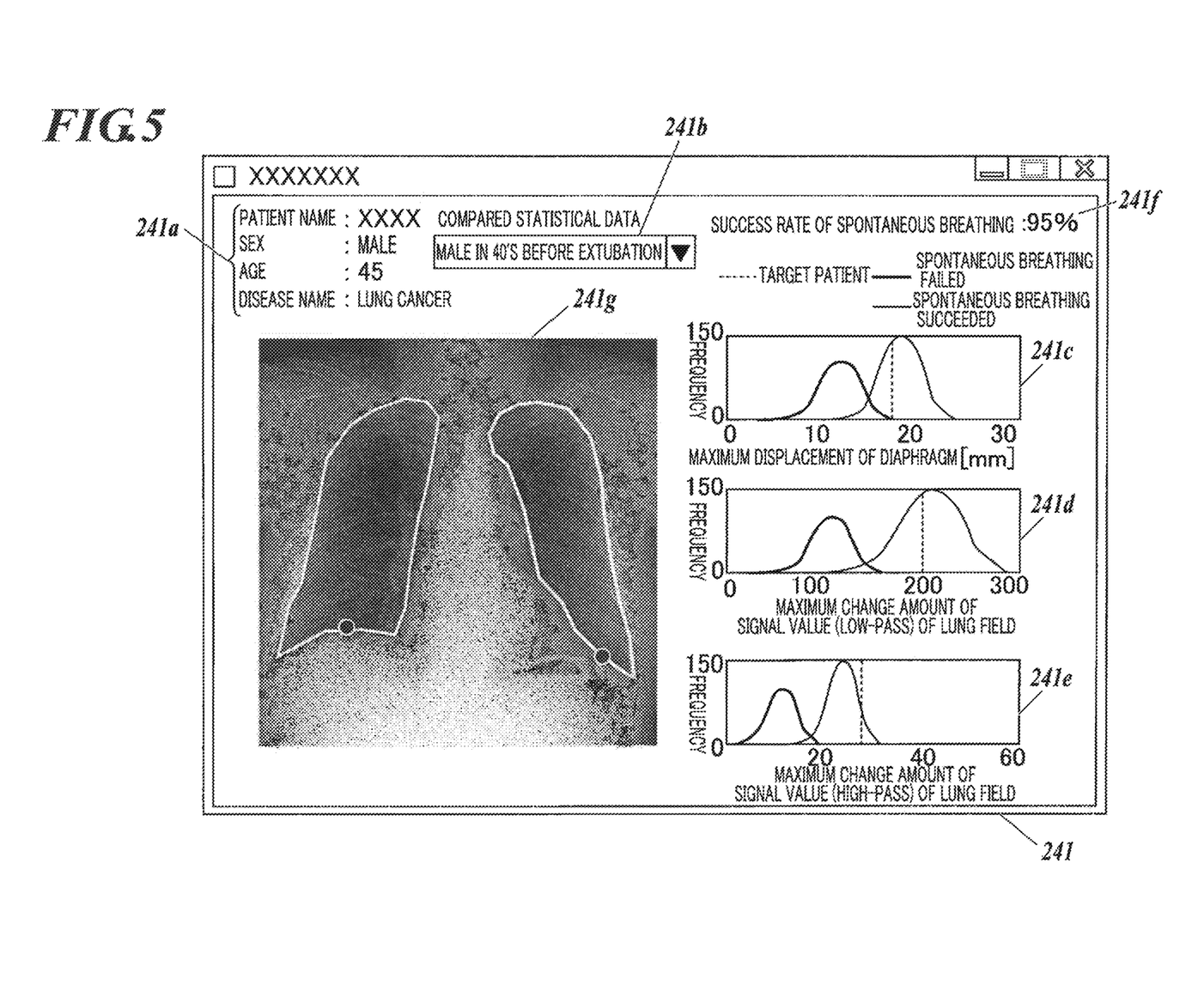
FIG. 5 shows an example of an assessment screen according to a first embodiment.

FIG. 5 shows an example of the assessment screen 241. As shown in FIG. 5, on the assessment screen 241, there are displayed patient information 241a about the examinee H, a category 241b of the compared statistic data, a comparison result 241c with the statistical data of the shape change amount of the predetermined structure, a comparison result 241d with the statistical data of the signal value change amount of the ventilation component, a comparison result 241e with the statistical data of the signal value change amount of the perfusion component, a breathing success rate 241f and a dynamic image 241g. FIG. 5 shows an example of comparison of the shape change amount (maximum displacement of the diaphragm) and the signal value change amounts of the lung fields calculated on the basis of the dynamic image 241f taken before extubation with the statistical data about patients who are the same generation and sex as the examinee H.

For example, if the breathing assessment item input in Step S1 is "before intubation", on the assessment screen 241, as the assessment information to assess the respiratory status of the examinee H at the time of intubation, positions of the shape change amount of the predetermined structure and the signal value change amounts of the lung fields before intubation about the examinee H are displayed on the distributions of the shape change amount of the predetermined structure and the signal value change amounts of the lung fields before intubation about the patients who have the same attribute information and/or vital information as the examinee H and have succeeded in ventilator breathing and the patients who have the same attribute information and/or vital information as the examinee H and have failed in ventilator breathing. Hence, a user can objectively understand in which one of the successful case and the failure case of ventilator breathing in the past, the shape change amount of the predetermined structure and the signal value change amounts before intubation about the examinee H falls, and accordingly can objectively assess whether the examinee H should be intubated. Further, displaying, in addition to the above, the success rate of ventilator breathing calculated on the basis of the dynamic image for the examinee H if intubated on the assessment screen 241 can reduce variation in the assessment among users and realize robust assessment.

For example, if the breathing assessment item input in Step S1 is "after intubation", on the assessment screen 241, as the assessment information to assess the respiratory status of the examinee H at the time of intubation, positions of the shape change amount of the predetermined structure and the signal value change amounts of the lung fields after intubation about the examinee H are displayed on the distributions of the shape change amount of the predetermined structure and the signal value change amounts of the lung fields after intubation about the patients who have the same attribute information and/or vital information as the examinee H and have succeeded in ventilator breathing and the patients who have the same attribute information and/or vital information as the examinee H and have failed in ventilator breathing. Hence, a user can objectively understand in which one of the successful case and the failure case of ventilator breathing in the past, the shape change amount of the predetermined structure and the signal value change amounts after intubation about the examinee H falls, and accordingly can objectively assess whether intubation of the examinee H has succeeded. Further, displaying, in addition to the above, the success rate of ventilator breathing calculated on the basis of the dynamic image on the assessment screen 241 can reduce variation in the assessment among users and realize robust assessment.

For example, if the breathing assessment item input in Step S1 is "before extubation", on the assessment screen 241, as the assessment information to assess the respiratory status of the examinee H at the time of extubation, positions of the shape change amount of the predetermined structure and the signal value change amounts of the lung fields before extubation about the examinee H are displayed on the distributions of the shape change amount of the predetermined structure and the signal value change amounts of the lung fields before extubation about the patients who have the same attribute information and/or vital information as the examinee H and have succeeded in spontaneous breathing after extubation and the patients who have the same attribute information and/or vital information as the examinee H and have failed in spontaneous breathing after extubation. Hence, a user can objectively understand in which one of the successful case and the failure case of spontaneous breathing after extubation in the past, the shape change amount of the predetermined structure and the signal value change amounts before extubation about the examinee H falls, and accordingly can objectively assess whether the examinee H should be extubated. Further, displaying, in addition to the above, the success rate of spontaneous breathing calculated on the basis of the dynamic image for the examinee H if extubated on the assessment screen 241 can reduce variation in the assessment among users and realize robust assessment.

For example, if the breathing assessment item input in Step S1 is "after extubation", on the assessment screen 241, as the assessment information to assess the respiratory status of the examinee H at the time of extubation, positions of the shape change amount of the predetermined structure and the signal value change amounts of the lung fields after extubation about the examinee H are displayed on the distributions of the shape change amount of the predetermined structure and the signal value change amounts of the lung fields after extubation about the patients who have the same attribute information and/or vital information as the examinee H and have succeeded in spontaneous breathing after extubation and the patients who have the same attribute information and/or vital information as the examinee H and have failed in spontaneous breathing after extubation. Hence, a user can objectively understand in which one of the successful case and the failure case of spontaneous breathing after extubation in the past, the shape change amount of the predetermined structure and the signal value change amounts after extubation about the examinee H falls, and accordingly can objectively assess whether extubation of the examinee H has succeeded. Further, displaying, in addition to the above, the success rate of spontaneous breathing after extubation calculated on the basis of the dynamic image on the assessment screen 241 can reduce variation in the assessment among users and realize robust assessment.

Second Embodiment

Next, a second embodiment is described.

Figure 6:
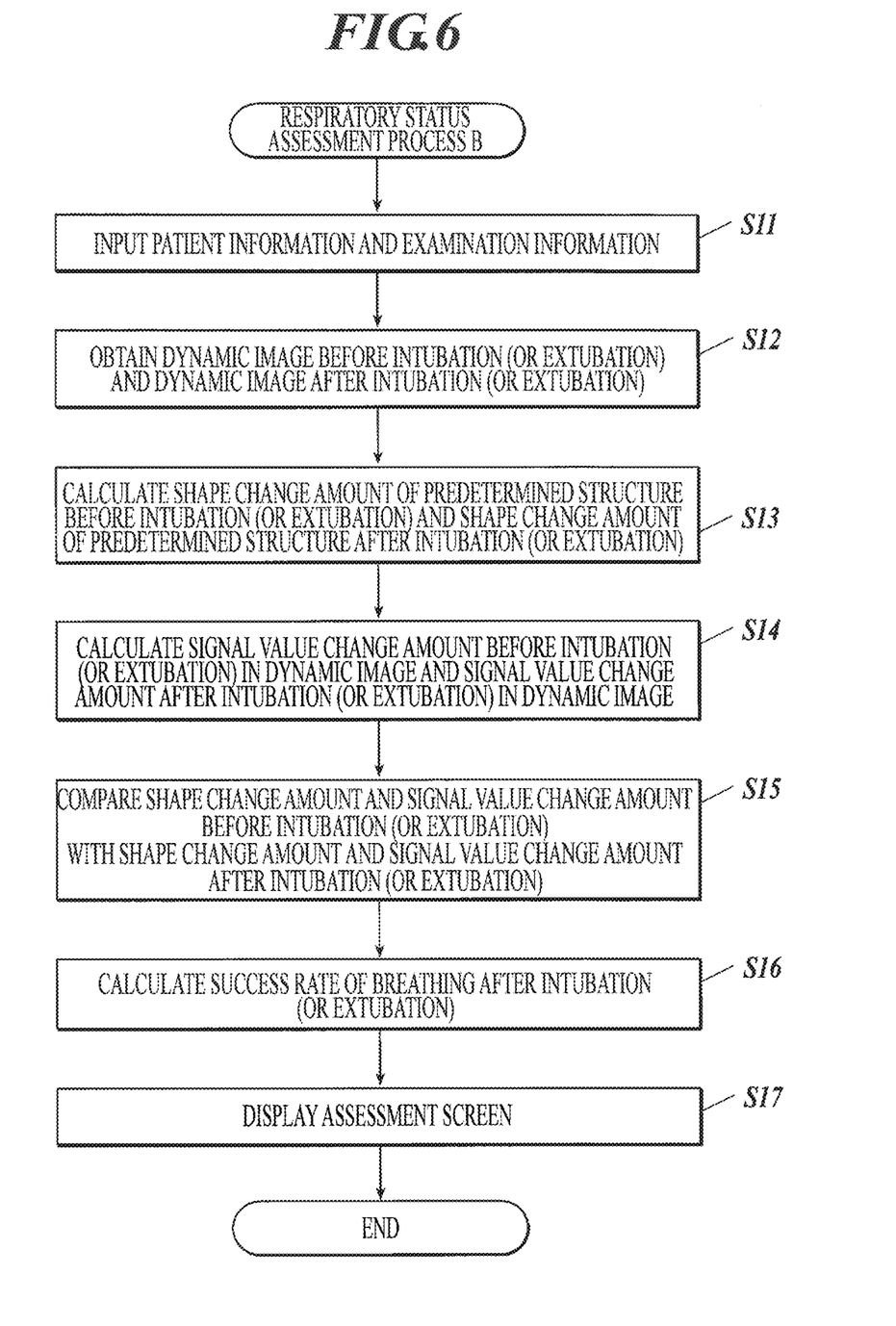
FIG. 6 is a flowchart of a respiratory status assessment process B that is performed by the controller shown in FIG. 2.

In the second embodiment, the storage 22 of the console 2 stores therein programs including a program to perform a respiratory status assessment process B shown in FIG. 6. Other than this, the configuration of the dynamic analysis system in the second embodiment is the same as that described in the first embodiment. Hence, description thereof is not repeated here, and actions in the second embodiment are described hereinafter.

FIG. 6 shows flow of the respiratory status assessment process B that is performed by the console 2 in the second embodiment. The respiratory status assessment process B is performed by the controller 21 working together with the program(s) stored in the storage 22.

In the respiratory status assessment process B, first, the controller 21 accepts inputs of patient information (name, age, sex, disease, etc.), and examination information (site to be examined (here, the chest), breathing assessment item (change before and after intubation, change before and after extubation), etc.) about an examinee H from the operation unit 23 (Step S11).

Next, the controller 21 controls the radiation emission controller 12 and the FPD cassette 4 so that dynamic imaging of the chest of the examinee H is performed in response to presses on the exposure switch 13, and obtains dynamic images each composed of a series of frame images (Step S12).

If the breathing assessment item input in Step S11 is "change before and after intubation", in Step S12, dynamic imaging of the examinee H is performed for several respiratory cycles immediately before the examinee H is intubated and for several respiratory cycles immediately after the examinee H is intubated. If the breathing assessment item input in Step S11 is "change before and after extubation", in Step S12, dynamic imaging of the examinee H is performed for several respiratory cycles immediately before the examinee H is extubated and for several respiratory cycles immediately after the examiner H is extubated.

To the examinee H, a vital information obtaining apparatus(es), such as a pulse oximeter, a sphygmomanometer and/or a respiration sensor, is attached to measure the vital information ($SpO_2$ value, $PaO_2$ value, heart rate, blood pressure value, respiratory rate, etc.) about the examinee H at the time of dynamic imaging. The measured vital information is input to the console 2 through wireless communications or the like.

A series of frame images of each dynamic image obtained by dynamic imaging is associated and stored with an identification ID to identify the dynamic image, the patient information, the examination information, the radiation emission conditions, the image reading conditions, the vital information at the time of dynamic imaging, the respective numbers indicating what number in the imaging order the respective frame images have been taken, and so forth in the storage 22.

Next, the controller 21 calculates the shape change amount of a predetermined structure of the chest of the examinee H in each obtained dynamic image (Step S13).

If the breathing assessment item input in Step S11 is "change before and after intubation", in Step S13, the controller 21 calculates, on the basis of the dynamic image taken before intubation, the shape change amount of the predetermined structure before intubation, and also calculates, on the basis of the dynamic image taken after intubation, the shape change amount of the predetermined structure after intubation. If the breathing assessment item input in Step S11 is "change before and after extubation", in Step S13, the controller 21 calculates, on the basis of the dynamic image taken before extubation, the shape change amount of the predetermined structure before extubation, and also calculates, on the basis of the dynamic image taken after extubation, the shape change amount of the predetermined structure after extubation. The method for calculating the shape change amount(s) of the predetermined structure is the same as that described in Step S3 in FIG. 3, and hence description thereof is not repeated here.

Next, the controller 21 calculates the signal value change amounts in the obtained dynamic images (Step S14).

If the breathing assessment item input in Step S11 is "change before and after intubation", in Step S14, the controller 21 calculates, on the basis of the dynamic image taken before intubation, the signal value change amounts before intubation, and also calculates, on the basis of the dynamic image taken after intubation, the signal value change amounts after intubation. If the breathing assessment item input in Step S11 is "change before and after extubation", in Step S14, the controller 21 calculates, on the basis of the dynamic image taken before extubation, the signal value change amounts before extubation, and also calculates, on the basis of the dynamic image taken after extubation, the signal value change amounts after extubation. The methods for calculating the signal value change amounts are the same as those described in Step S4 in FIG. 3, and hence descriptions thereof are not repeated here.

Next, the controller 21 compares the shape change amount and the signal value change amounts before intubation (or extubation) with the shape change amount and the signal value change amounts after intubation (or extubation), which are calculated in Steps S13 and S14 (Step S15).

For example, if the breathing assessment item input in Step S11 is "change before and after intubation", the controller 21 plots, on the scale of the same numerical value axis, the shape change amount calculated from the dynamic image taken before intubation and the shape change amount calculated from the dynamic image taken after intubation. Further, the controller 21 plots, on the scale of the same numerical value axis, each signal value change amount calculated from the dynamic image taken before intubation and its corresponding signal value change amount calculated from the dynamic image taken after intubation.

If the breathing assessment item input in Step S11 is "change before and after extubation", the controller 21 plots, on the scale of the same numerical value axis, the shape change amount calculated from the dynamic image taken before extubation and the shape change amount calculated from the dynamic image taken after extubation. Further, the controller 21 plots, on the scale of the same numerical value axis, each signal value change amount calculated from the dynamic image taken before extubation and its corresponding signal value change amount calculated from the dynamic image taken after extubation.

Next, the controller 21 calculates the success rate of breathing after intubation (or extubation) for the examinee H with a machine learning classifier of deep neural networks or the like (Step S16).

For example, if the breathing assessment item input in Step S11 is "change before and after intubation", the controller 21 calculates the success rate of ventilator breathing for the examinee H by inputting the attribute information obtained in Step S11 and/or the vital information obtained in Step S12, and the shape change amounts and/or the signal value change amounts before and after intubation calculated in Step S13 and Step S14, respectively, about the examinee H, into the classifier of deep neural networks or the like trained with, as feature amounts, the attribute information and/or the vital information at the time of intubation, the shape change amounts and/or the signal value change amounts before and after intubation, and data of the success/failure result of ventilator breathing about each patient who has been intubated in the past.

For example, if the breathing assessment item input in Step S11 is "change before and after extubation", the controller 21 calculates the success rate of spontaneous breathing after extubation for the examinee H by inputting the attribute information obtained in Step S11 and/or the vital information obtained in Step S12, and the shape change amounts and/or the signal value change amounts before and after extubation calculated in Step S13 and Step S14, respectively, about the examinee H, into the classifier of deep neural networks or the like trained with, as feature amounts, the attribute information and/or the vital information at the time of extubation, the shape change amounts and/or the signal value change amounts before and after extubation, and data of the success/failure result of spontaneous breathing after extubation about each patient who has been extubated in the past.

Next, the controller 21 displays, on the display 24, an assessment screen 242 that contains the comparison result in Step S15 and the calculation result in Step S16 (Step S17), and ends the respiratory status assessment process B.

Figure 7:
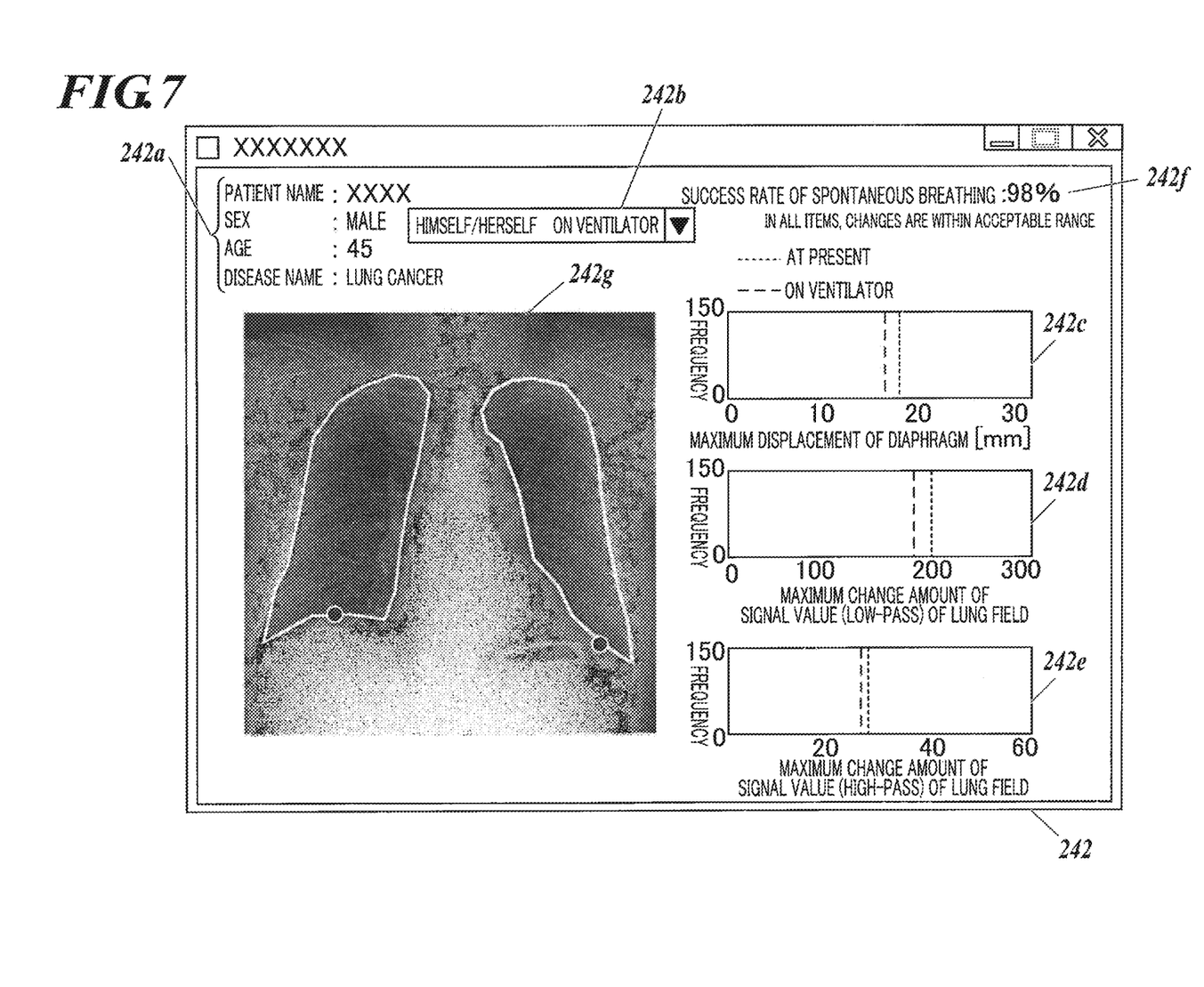
FIG. 7 shows an example of an assessment screen according to a second embodiment.

FIG. 7 shows an example of the assessment screen 242. As shown in FIG. 7, on the assessment screen 242, there are displayed patient information 242a about the examinee H, a category 242b of the compared data, a comparison result 242c between the shape change amounts of the predetermined structure before and after intubation (or extubation), a comparison result 242d between the signal value change amounts of the ventilation component before and after intubation (or extubation), a comparison result 242e between the signal value change amounts of the perfusion component before and after intubation (or extubation), a breathing success rate 242f and a dynamic image 242g. FIG. 7 shows the shape change amount and the signal value change amounts of the lung fields after extubation (at present) calculated on the basis of the dynamic image 242g in such a way as to be compared with those before extubation (on ventilator).

For example, if the breathing assessment item input in Step S11 is "change before and after intubation", on the assessment screen 242, as the assessment information to assess the respiratory status of the examinee H at the time of intubation, the shape change amount and the signal value change amounts calculated from the dynamic image taken before intubation and the shape change amount and the signal value change amounts calculated from the dynamic image taken after intubation are displayed by respectively being plotted on the scale of the same numerical value axis. Hence, a user can objectively and readily assess change in the respiratory status of the examinee H (e.g. whether a large difference is generated) before and after intubation. Further, displaying, in addition to the above, the success rate of ventilator breathing calculated on the basis of the dynamic images on the assessment screen 242 can reduce variation in the assessment among users and realize robust assessment.

For example, if the breathing assessment item input in Step S11 is "change before and after extubation", on the assessment screen 242, as the assessment information to assess the respiratory status of the examinee H at the time of extubation, the shape change amount and the signal value change amounts calculated from the dynamic image taken before extubation and the shape change amount and the signal value change amounts calculated from the dynamic image taken after extubation are displayed by respectively being plotted on the scale of the same numerical value axis. Hence, a user can objectively and readily assess change in the respiratory status of the examinee H (e.g. whether a large difference is generated) before and after extubation. Further, displaying, in addition to the above, the success rate of spontaneous breathing after extubation calculated on the basis of the dynamic images on the assessment screen 242 can reduce variation in the assessment among users and realize robust assessment.

Although the first and second embodiments of the invention are described above, the matters described in the above embodiments are merely some of preferred examples of the dynamic analysis system of the invention, and not intended to limit the invention.

For example, in the above embodiments, the dynamic analysis system is a visiting system. However, the invention is applicable to a dynamic analysis system that performs imaging in an imaging room and analyzes the obtained dynamic image(s).

Further, in the above embodiments, on the basis of the dynamic image(s), both the signal value change amounts and the shape change amount(s) of a predetermined structure are calculated and used for assessment of the respiratory status at the time of intubation or extubation. Alternatively, either the signal value change amount(s) or the shape change amount(s) may be calculated and used for assessment of the respiratory status at the time of intubation or extubation.

Further, in the above embodiments, the statistical data are stored in the storage 22 beforehand. Alternatively, the statistical data of the signal value change amounts and the shape change amount about the patients who have the same attribute information and/or vital information as the examinee H may be generated at the time of comparison in Step S5 or Step S15 on the basis of the patient information, the vital information at the time of dynamic imaging, and data indicating the success/failure result of ventilator breathing after intubation or spontaneous breathing after extubation about each patient who has been imaged in the past at the time of intubation or extubation, which are stored in the storage 22.

Further, in the above, as a computer readable medium for the programs of the invention, a hard disk, a nonvolatile semiconductor memory or the like is used. However, the computer readable medium is not limited thereto. For example, as the computer readable medium, a portable recording medium, such as a CD-ROM, can also be used. Further, as a medium to provide data of the programs of the invention, a carrier wave can be used.

In addition to the above, the specific configurations/components and the specific actions of the apparatuses of the dynamic analysis system can also be appropriately modified without departing from the spirit of the invention.

Although some embodiments of the invention have been described and illustrated in detail, the disclosed embodiments are made for purposes of illustration and example only and not limitation. The scope of the invention should be interpreted by terms of the appended claims.

The entire disclosure of Japanese Patent Application No. 2017-025509 filed on Feb. 15, 2017 is incorporated herein by reference in its entirety.

What is claimed is:

1. A dynamic analysis system comprising a hardware processor that:
   based on a first plurality of frame images showing a dynamic state of a chest of an intubated first examinee obtained by radiation imaging of the chest of the first examinee, calculates a signal value change amount and/or a shape change amount of a predetermined structure of the chest in the first plurality of frame images;
   based on the calculated signal value change amount and/or shape change amount, generates assessment information to assess a respiratory status of the first examinee at time of intubation or extubation;
   obtains attribute information and/or vital information at the time of intubation about the first examinee; and
   into a machine learning classifier constructed based on the signal value change amount and/or the shape change amount and the attribute information and/or the vital information at the time of intubation and a success/failure result of ventilator breathing about a second examinee, inputs the signal value change amount and/or the shape change amount and the attribute information and/or the vital information at the time of intubation about the first examinee, and calculates a success rate of the ventilator breathing for the first examinee, thereby generating the assessment information to assess the respiratory status of the first examinee at the time of intubation.

2. A dynamic analysis system comprising a hardware processor that:
   based on a first plurality of frame images showing a dynamic state of a chest of an intubated first examinee obtained by radiation imaging of the chest of the first examinee, calculates a signal value change amount and/or a shape change amount of a predetermined structure of the chest in the first plurality of frame images;
   based on the calculated signal value change amount and/or shape change amount, generates assessment information to assess a respiratory status of the first examinee at time of intubation or extubation;
   obtains attribute information and/or vital information at the time of extubation about the first examinee; and
   into a machine learning classifier constructed based on the signal value change amount and/or the shape change amount and the attribute information and/or the vital information at the time of extubation and a success/failure result of spontaneous breathing after extubation about a second examinee, inputs the signal value change amount and/or the shape change amount and the attribute information and/or the vital information at the time of extubation about the first examinee, and calculates a success rate of spontaneous breathing after extubation for the first examinee, thereby generating the assessment information to assess the respiratory status of the first examinee at the time of extubation.

3. A dynamic analysis system comprising a hardware processor that:

based on a first plurality of frame images showing a dynamic state of a chest of an intubated first examinee obtained by radiation imaging of the chest of the first examinee, calculates a signal value change amount and/or a shape change amount of a predetermined structure of the chest in the first plurality of frame images;

based on the calculated signal value change amount and/or shape change amount, generates assessment information to assess a respiratory status of the first examinee at time of intubation or extubation;

based on a second plurality of frame images showing the dynamic state of the chest of the first examinee before intubation, calculates the signal value change amount and/or the shape change amount before intubation about the first examinee;

based on the first plurality of frame images showing the dynamic state of the chest of the first examinee after intubation, calculates the signal value change amount and/or the shape change amount after intubation about the first examinee; and based on the calculated signal value change amount and/or shape change amount before intubation and the calculated signal value change amount and/or shape change amount after intubation about the first examinee, generates the assessment information to assess the respiratory status of the first examinee at the time of intubation.

4. The dynamic analysis system according to claim 3, wherein the hardware processor compares the calculated signal value change amount and/or shape change amount before intubation with the calculated signal value change amount and/or shape change amount after intubation, thereby generating a result of the comparison as the assessment information to assess the respiratory status of the first examinee at the time of intubation.

5. The dynamic analysis system according to claim 3, wherein the hardware processor:
   obtains attribute information and/or vital information at the time of intubation about the first examinee; and
   into a machine learning classifier constructed based on the signal value change amounts and/or the shape change amounts before and after intubation, the attribute information and/or the vital information at the time of intubation and a success/failure result of ventilator breathing about a second examinee, inputs the signal value change amounts and/or the shape change amounts before and after intubation and the attribute information and/or the vital information at the time of intubation about the first examinee, and calculates a success rate of the ventilator breathing for the first examinee, thereby generating the assessment information to assess the respiratory status of the first examinee at the time of intubation.

6. A dynamic analysis system comprising a hardware processor that:
   based on a first plurality of frame images showing a dynamic state of a chest of an intubated first examinee obtained by radiation imaging of the chest of the first examinee, calculates a signal value change amount and/or a shape change amount of a predetermined structure of the chest in the first plurality of frame images;
   based on the calculated signal value change amount and/or shape change amount, generates assessment information to assess a respiratory status of the first examinee at time of intubation or extubation;
   based on the first plurality of frame images showing the dynamic state of the chest of the first examinee before extubation, calculates the signal value change amount and/or the shape change amount before extubation about the first examinee;
   based on a second plurality of frame images showing the dynamic state of the chest of the first examinee after extubation, calculates the signal value change amount and/or the shape change amount after extubation about the first examinee; and
   based on the calculated signal value change amount and/or shape change amount before extubation and the calculated signal value change amount and/or shape change amount after extubation about the first examinee, generates the assessment information to assess the respiratory status of the first examinee at the time of extubation.

7. The dynamic analysis system according to claim 6, wherein the hardware processor compares the calculated signal value change amount and/or shape change amount before extubation with the calculated signal value change amount and/or shape change amount after extubation, thereby generating a result of the comparison as the assessment information to assess the respiratory status of the first examinee at the time of extubation.

8. The dynamic analysis system according to claim 6, wherein the hardware processor:
   obtains attribute information and/or vital information at the time of extubation about the first examinee; and
   into a machine learning classifier constructed based on the signal value change amounts and/or the shape change amounts before and after extubation, the attribute information and/or the vital information at the time of extubation and a success/failure result of spontaneous breathing after extubation about a second examinee, inputs the signal value change amounts and/or the shape change amounts before and after extubation and the attribute information and/or the vital information at the time of extubation about the first examinee, and calculates a success rate of the spontaneous breathing after extubation for the first examinee, thereby generating the assessment information to assess the respiratory status of the first examinee at the time of extubation.

9. A dynamic analysis system comprising a hardware processor that:
   based on a first plurality of frame images showing a dynamic state of a chest of an intubated first examinee obtained by radiation imaging of the chest of the first examinee, calculates a signal value change amount and/or a shape change amount of a predetermined structure of the chest in the first plurality of frame images;
   performs a comparison of the calculated at least one of the signal value change amount and the shape change amount with statistical data of the at least one of the signal value change amount and the shape change amount calculated about a second examinee; and
   based on the comparison, generates assessment information to assess a respiratory status of the first examinee at time of intubation or extubation,
   wherein the statistical data used in generating the assessment information to assess the respiratory status of the first examinee at the time of intubation includes statistical data of the at least one of the signal value change amount and the shape change amount about the second examinee who has succeeded in ventilator breathing and statistical data of the at least one of the signal value change amount and the shape change amount about the second examinee who has failed in the ventilator breathing; and/or wherein the statistical data used in generating the assessment information to assess the respiratory status of the first examinee at the time of extubation includes statistical data of the at least one of the signal value change amount and the shape change amount about the second examinee who has succeeded in spontaneous breathing after extubation and statistical data of the at least one of the signal value change amount and the shape change amount about the second examinee who has failed in the spontaneous breathing after extubation.

10. The dynamic analysis system according to claim 9, wherein the hardware processor:

obtains attribute information and/or vital information at the time of intubation or extubation about the first examinee; and compares the calculated signal value change amount and/or shape change amount with the statistical data of the signal value change amount and/or the shape change amount calculated about the second examinee who has the same attribute information and/or vital information as the first examinee, thereby generating the result of the comparison as the assessment information to assess the respiratory status of the first examinee at the time of intubation or extubation.

11. The dynamic analysis system according to claim 9, wherein the statistical data used in generating the assessment information to assess the respiratory status of the first examinee at the time of intubation includes the statistical data of the signal value change amount and/or the shape change amount about the second examinee who has succeeded in ventilator breathing and the statistical data of the signal value change amount and/or the shape change amount about the second examinee who has failed in the ventilator breathing.

12. The dynamic analysis system according to claim 9, wherein the statistical data used in generating the assessment information to assess the respiratory status of the first examinee at the time of extubation includes the statistical data of the signal value change amount and/or the shape change amount about the second examinee who has succeeded in spontaneous breathing after extubation and the statistical data of the signal value change amount and/or the shape change amount about the second examinee who has failed in the spontaneous breathing after extubation.

* * * * *